(12) United States Patent
Yan (10) Patent No.: US 8,850,895 B2
(45) Date of Patent: Oct. 7, 2014

(54) UNPOWERED, WIRELESS PRESSURE SENSOR FOR POINT-OF-CARE GLAUCOMA DIAGNOSIS

(75) Inventor: John Yan, Foster City, CA (US)

(73) Assignee: John Yan, Foster City, CA (US)

(*) Notice: Subject to any disclaimer, the term of this patent is extended or adjusted under 35 U.S.C. 154(b) by 337 days.

(21) Appl. No.: 13/330,681

(22) Filed: Dec. 20, 2011

(65) Prior Publication Data
US 2013/0055819 A1 Mar. 7, 2013

Related U.S. Application Data

(60) Provisional application No. 61/530,940, filed on Sep. 3, 2011.

(51) Int. Cl.
*G01L 9/00* (2006.01)
*A61B 3/16* (2006.01)

(52) U.S. Cl.
CPC ........................................ *A61B 3/16* (2013.01)
USPC ............................................. 73/705; 73/715

(58) Field of Classification Search
None
See application file for complete search history.

(56) References Cited

U.S. PATENT DOCUMENTS

| | | | |
|---|---|---|---|
| 6,645,432 B1* | 11/2003 | Anderson et al. | 422/502 |
| 6,686,184 B1* | 2/2004 | Anderson et al. | 435/174 |
| 7,267,938 B2* | 9/2007 | Anderson et al. | 435/4 |
| 7,670,556 B2* | 3/2010 | Corn et al. | 422/68.1 |
| 7,835,013 B2* | 11/2010 | Jones et al. | 356/517 |
| 7,887,508 B2* | 2/2011 | Meng et al. | 604/114 |
| 8,088,615 B2* | 1/2012 | Ausserre | 435/287.2 |
| 8,124,029 B2* | 2/2012 | Polwart et al. | 422/502 |
| 8,308,686 B2* | 11/2012 | Meng et al. | 604/114 |
| 2011/0015512 A1* | 1/2011 | Pan et al. | 600/399 |

* cited by examiner

*Primary Examiner* — Lisa Caputo
*Assistant Examiner* — Jermaine Jenkins (57) ABSTRACT

The disclosed invention describes an unpowered apparatus which can wirelessly sense pressure based on microfluidics for point-of-care glaucoma diagnosis. Moreover, the disclosed invention teaches methods to construct the invention using microfabrication processing. Finally, a detailed and illustrative schematic of the wireless readout system is disclosed.

8 Claims, 7 Drawing Sheets

UNPOWERED, WIRELESS PRESSURE SENSOR FOR POINT-OF-CARE GLAUCOMA DIAGNOSIS

RELATED APPLICATIONS

The presented application is a continuation-in-part of U.S. patent application Ser. No. 61/530,940, Filed Sep. 3, 2011, entitled, "An Unpowered, Wireless Contact Lens Pressure Sensor for Point-of-Care Glaucoma Diagnosis."

BACKGROUND OF THE INVENTION

Glaucoma is a group of ocular diseases which is believed to develop as a result of an increase in ocular pressure that pinches the optic nerve at the back of the retina, and affects tens of millions of people worldwide. Those affected by glaucoma may experience gradual loss in their peripheral vision. Glaucoma has been nicknamed the "silent thief of sight" because the loss of vision occurs gradually over a long period of time and is often only recognized when the disease is quite advanced. Once the visual field is lost, the damage cannot be recovered. Moreover, lab-on-a-chip (LOC) technology pertains to a device that integrates one or more laboratory functions on a single chip of only millimeters to a few square centimeters in size and pertains to the handling of extremely small fluid volumes down to a less than pico litters. LOC field more and more exceeds the borders between lithography-based microsystem technology, nano technology and precision engineering for added system value and is believed to become an important part of the efforts to improve global health through the development of point-of-care testing devices.

As we move into the world of distributed, ubiquitous computing, sensors will play an increasing role in interfacing between the digital world and the real world. Specifically for glaucoma diagnosis, a low-cost, unpowered wireless sensor which can immediately detect changes in intraocular pressure is in great demand for rapid, point-of-care diagnosis, since early detection can quickly prevent irreversible damage to human vision. In even higher demand is a sensor which can be directly integrated with existing wireless infrastructure.

Prior art in the development of wireless pressure sensor have employed inductor-capacitor coupling techniques, microfabricated strain gauges, complementary metal oxide semiconductor (CMOS) based technologies and other radio frequency powered which often employ nonbiocompatible metals, complicated manufacturing processing and materials. To the best of the inventors' knowledge, no unpowered, wireless pressure sensor which employs a microfluidic network to relate pressure to a corresponding fluidic displacement which can be consequently readout through an optical imaging system has been disclosed.

SUMMARY OF THE INVENTION

The disclosed invention is an unpowered apparatus which can wirelessly sense pressure based on microfluidics for point-of-care glaucoma diagnosis, methods to microfabricate the device and a corresponding wireless readout system. Such a sensor is composed of PDMS or PDMS-plastic composites consisting of a network large, deformable sensing chambers connected to a network of sensing channels with fluidic impedance transformers installed throughout the transitions. The sensing fluid has the properties of low vapour pressure and biocompatible. Moreover, the disclosed invention teaches methods to construct the invention using simple microfabrication processing with the most notable being an method to employ oxygen plasma treatment to create an oligomer bond between PDMS and plastic materials. Finally, a detailed and illustrative schematic of the wireless readout system is disclosed.

BRIEF DESCRIPTION OF THE DRAWING

FIG. 2 (A-E) pertains to a flow diagram of the techniques to micromachine the device.

DETAILED DESCRIPTION OF THE INVENTION

Figure 1A:
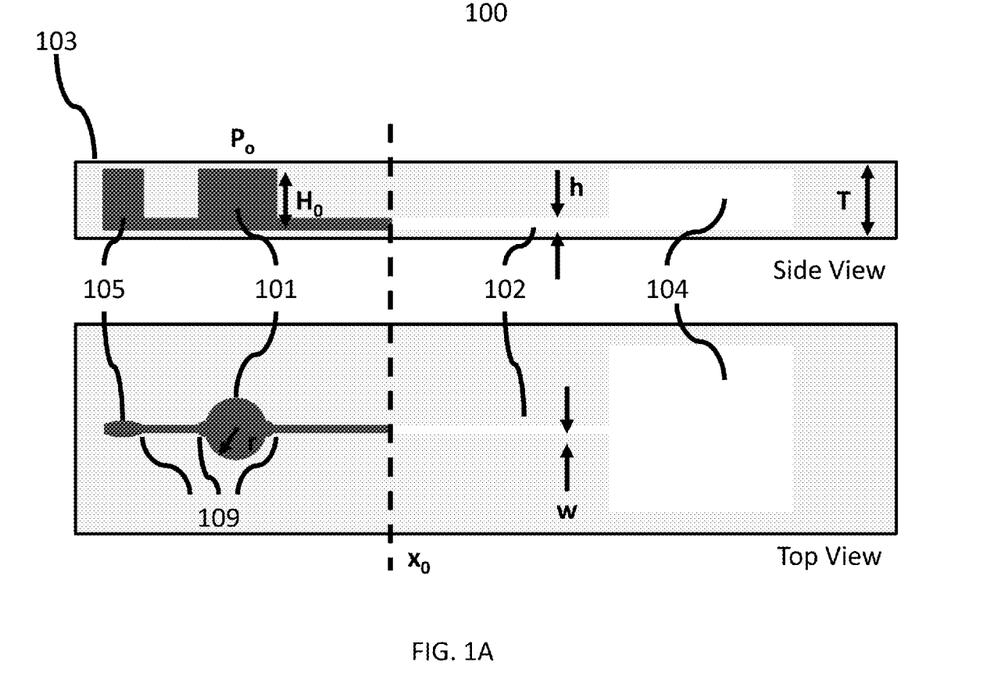
FIG. 1A is a schematic of the device operation.

Referring now to the invention in more detail, FIG. 1A illustrates of the sensing principle of the device from the top view and side view. (100) illustrates the device when no pressure ($P_o$) is applied to the device showing a fluidic at $x_o$. It consists of an injection port (105), a large network of sensing chambers (101), with height H and radius r, interconnected to narrow sensing channels (102), with height h and width w, followed by an out-flow chamber (104) encased in a polymer (103), with thickness T, such as, but not limited to, thermally crosslinked polydimethylsiloxane (PDMS) or PDMS-plastic composites. While (100) shows (102) as a straight sensing channels, meandered sensing channels (401) can also be micromachined. As pressure (P') is applied to the device, as illustrated in (110) in FIG. 1B, the large sensing chambers (111) deform more readily than the narrowing sensing channels displacing fluid (112) from the sensing chambers outward to x'. Herein, (114) acts as a pressure relief conduit due to its large volume compared to the sensing channels The displacement of fluid corresponds to a known pressure which can be detected through optical observation.

Figure 1B:
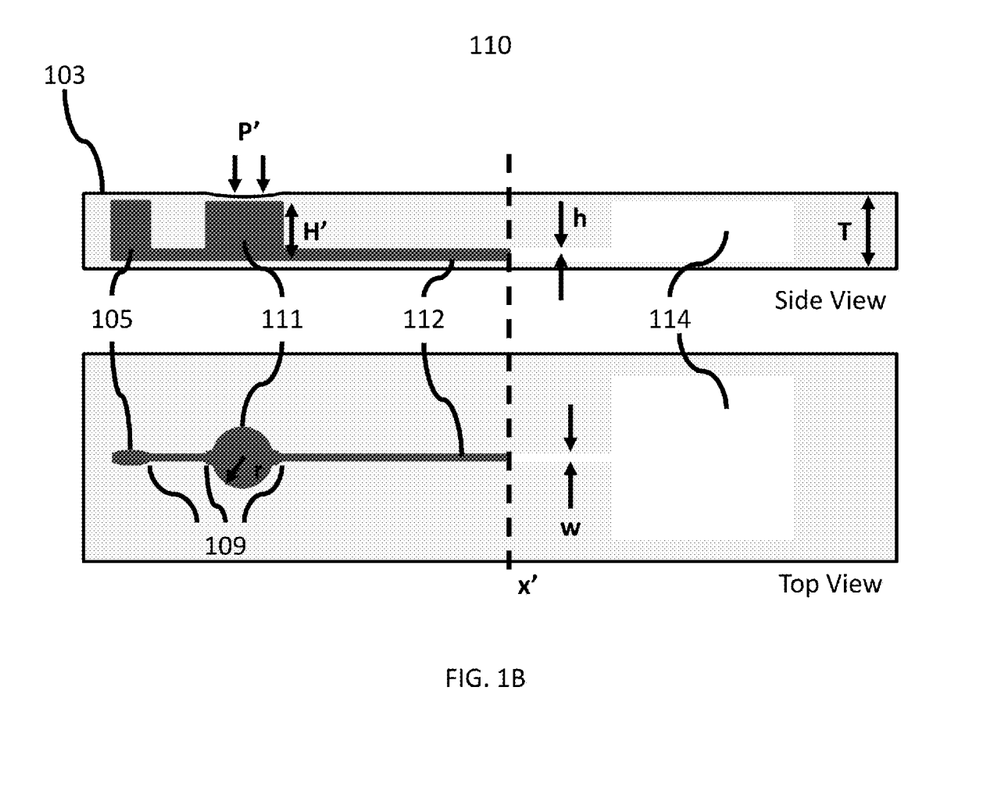
FIG. 1B is a schematic of the device operation.

The ratio of the H/h are drawn arbitrarily, as illustrated in FIG. 1(A-B), intentionally to illustrate that a variety of ratios can be employed to tune the sensitivity of the pressure sensor for different cases and topologies of the sensing chamber network and sensing channels.

Figure 1C:
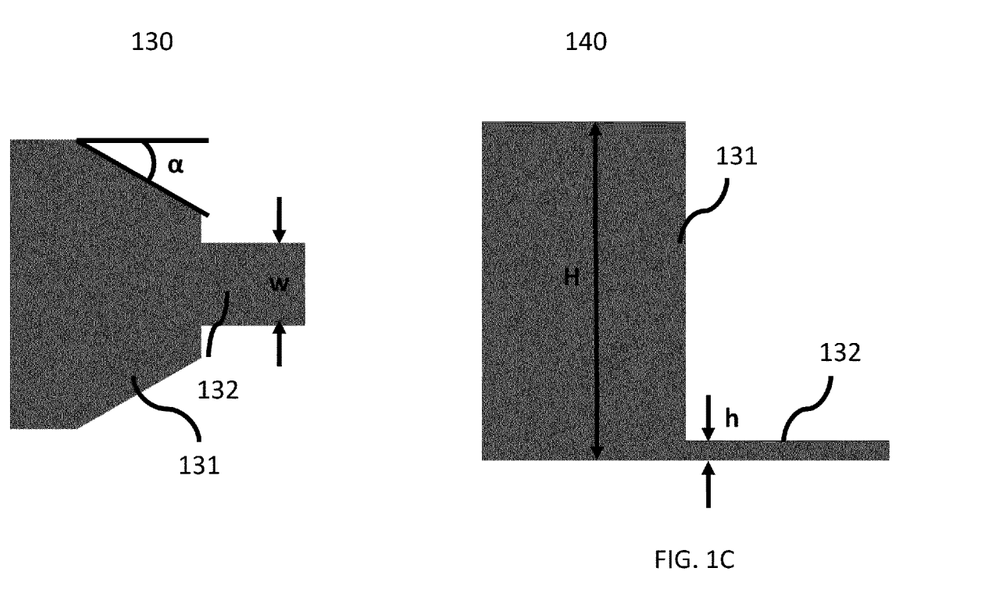
FIG. 1C is a detailed drawing of fluidic impedance transformer.
Figures 2A, 2B, 2D:
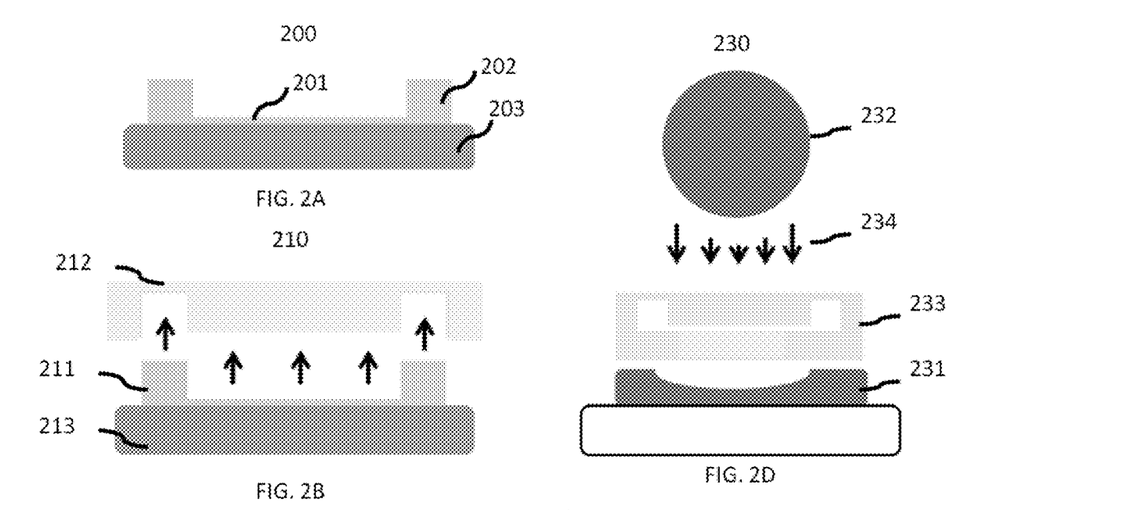
FIG. 2A pertains to the microfabrication of 3-D replica mold.
FIG. 2B pertains to the soft lithography process.
FIG. 2D pertains to the thermocompression process.
Figure 2C:
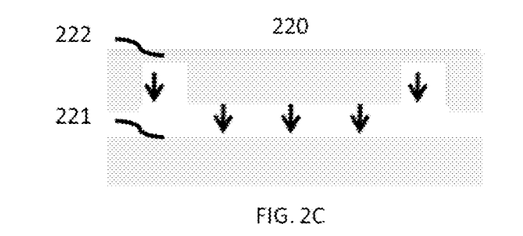
FIG. 2C pertains bonding process of the micromachined PDMS to another piece of PDMS or plastic block.
Figure 2E:
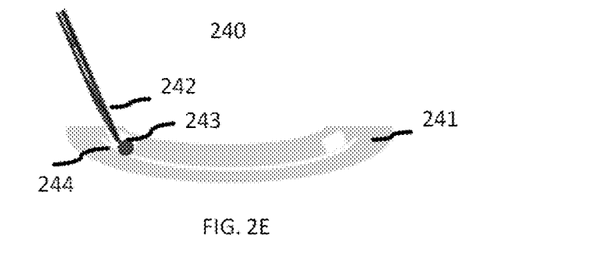
FIG. 2E pertains to the fluidic injection process.

One skilled in the art will recognize that to prevent gas cavitation during fluidic movement in the microfluidic network and the injection process, to be later described, a fluidic impedance transformer (109), as illustrated in FIG. 1C, needs to be installed. A detailed bird's eye and cross section view of the fluidic impedance transformer is shown in (130) and (140), respectively. The fluidic impedance transformer acts to gradually adjust the pressure within the microfluidic network from a low pressure region (131) to a high pressure region (132). An angle, α, is employed to prevent gas cavation at the entrances and exits of the taller and larger sensing chambers. Such a transformer is employed at (109) and throughout the embodied device as illustrated in (400).

In further detail and still referring to the invention, FIG. 2A-E, illustrates the flow diagram of the microfabrication process. The first step (200) to realize the elastomeric device is the 3-D replica mold (201-203). The 3-D replica mold can be constructed, but not limited to, photodefined negative tone photoresist (201-202) micromachining techniques where (201) refers to the first level and (202) refers to the second level of the replica mold. Other techniques include traditional computer numerical control (CNC) milling techniques, deep ion reactive etching (DRIE), laser lithography techniques, etc. Next (210), PDMS prepolymer is mixed, degassed and poured onto the 3-D master mold (211, 213) to thermally crosslink. The cured PDMS mold is subsequently removed from the master mold (212) is then (220) exposed to oxygen plasma treatment (222) to create radical hydroxyl groups on the surface to initiate the covalent bonding onto plastic surface (221) such as PDMS. The two bonded layers (233) of PDMS-plastic can then be thermocompressed (230) in a heated platform (231) in the shape of a contact lens. (234) illustrates the force applied to the rigid sphere (232) against the opposing mold. Finally, fluid (243) is injected into the microfluidic network encasing (241) through the injection port (244) by means of a narrow pointed syringe needle (242).

One skilled in the art will recognize various fluids with low vapour pressure and are biocompatible such as, but not limited to, glycerol and glycerol mixtures and ionic liquid and ionic liquid mixtures can be employed as the fluid. Furthermore, it is obvious to one skilled in the art that this is only one means by which the device can be micromachined and various other combinations can be employed without departing from the spirit of the invention.

Figure 3:
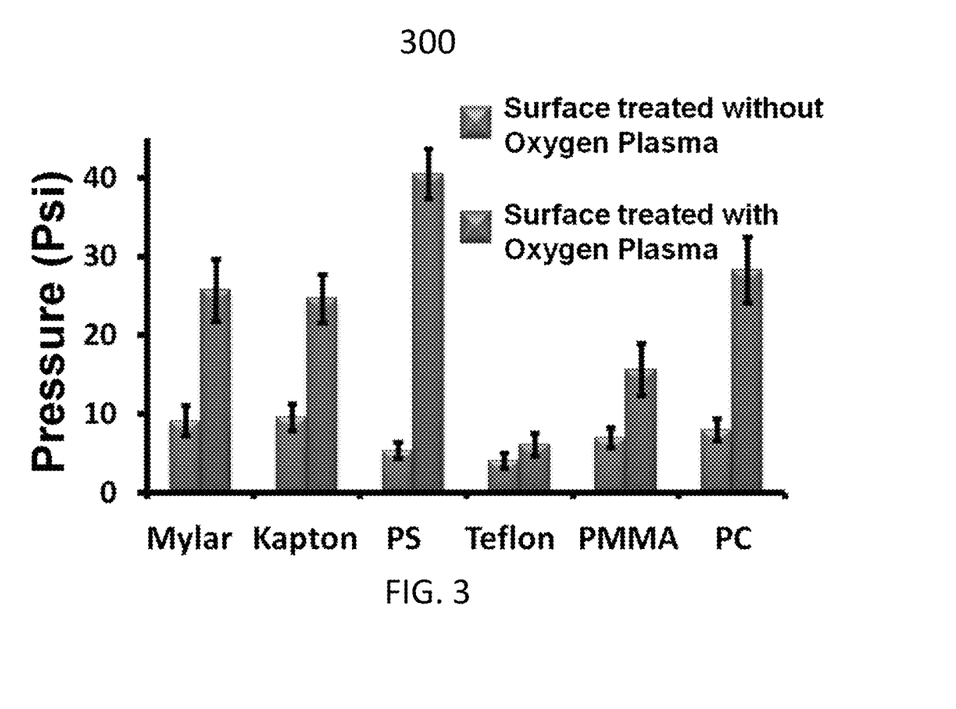
FIG. 3 illustrates a set of measured adhesion properties from various PDMS-plastic composites.

One skilled in the art will quickly realize that the device can be micromachined out of PDMS-plastic composites. Thus, it is obvious that a simple adhesion method to bond PDMS onto various plastics must be employed. While one skilled in the art can employ solvent assisted bonding, thermal bonding or chemical coupling agents using aminosiloxane chemistry, orthsilicate or other chemical vapour deposition process, the disclosed invention teaches a simple method to adhere PDMS-plastic composite-material devices. This process is to employ extended oxygen plasma treatment onto the plastic surface, followed by direction deposition of PDMS prepolymer, which can be patterned through photolithography or microConact printing process. An illustration of the adhesion improvement is shown in FIG. 3 where a variety of plastics, such as Mylar®, Kapton™ HN, polystyrene (PS), Teflon®, polycarbonate (PC) and poly(methyl methacrylate) (PMMA) and their corresponding adhesion strengths with and without the extended oxygen plasma treatment. In general, an adhesion improvement of 3× is observed for Mylar®, Kapton™ HN, PMMA and PC. Remarkably, PS showed an approximately 7× improvement. The adhesion of Teflon® showed minor improvements in adhesion. The proper oxygen plasma treatment time is critical to activate the plastic surface. Too much oxygen plasma treatment can potentially overheat the sample, causing it to warp, and should be avoided. Repeatability depends on optimizing the oxygen concentration in the plasma chamber, power, treatment time, operating frequency, distance from the electrode and plastic substrate. The adhesion strength of extended plasma treatment of plastic substrates and cured PDMS which is plasma activated showed poor adhesion.

Figure 4:
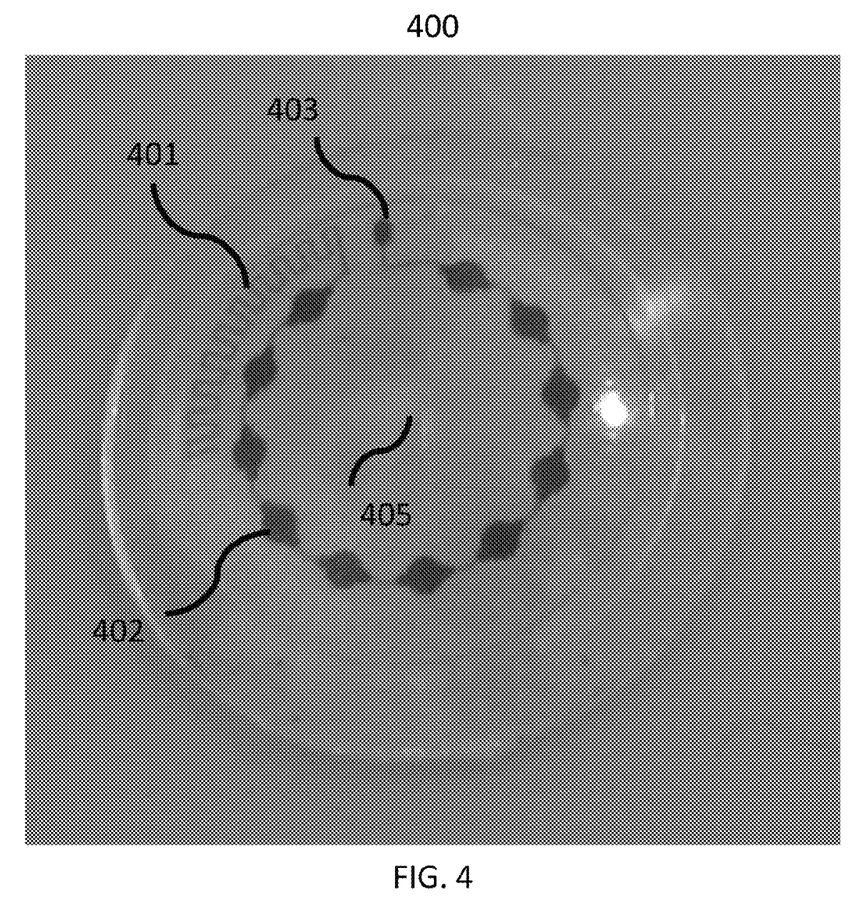
FIG. 4 illustrates a prototyped an unpowered, wireless pressure sensor based on microfluidics for point-of-care glaucoma diagnosis.
Figure 5:
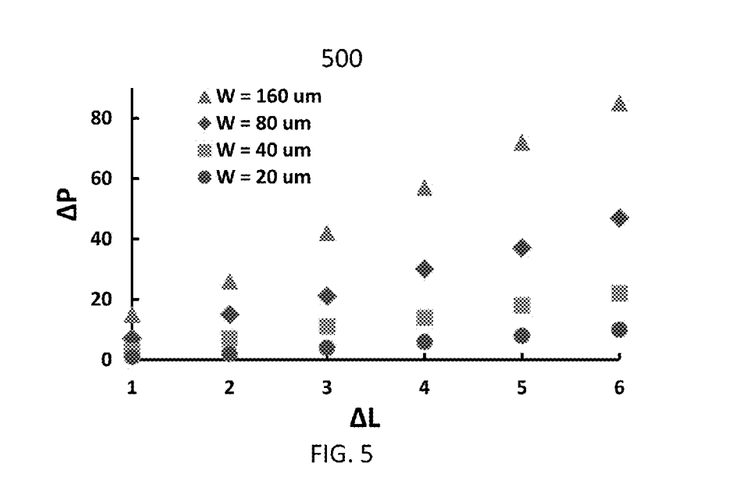
FIG. 5 illustrates a set of measured responses of the unpowered, wireless pressure sensor based on microfluidics for point-of-care glaucoma and other lab-on-a-chip applications with different widths.

In further detail and still referring to the invention, FIG. 4 illustrates a prototyped unpowered, wireless pressure sensor based on microfluidics for point-of-care glaucoma diagnosis. The previously described injection port (403), network of sensing chambers (402), sensing channels (401) are illustrated in the photographic image of the prototyped device. An optical, circular opening (405) is created such that the line of sight doesn't impede the pupil for visual sensation. In further detail and still referring the invention, FIG. 5 illustrates a set of measured responses of the unpowered, wireless pressure sensor based on microfluidics for point-of-care glaucoma and other lab-on-a-chip applications with different widths for a fixed sensing chamber geometry. The results illustrate that a variety of different mechanic-fluidic responses can be realized in the disclosed in the unpowered pressure sensor which can detected wirelessly in the embodied invention.

Figure 6:
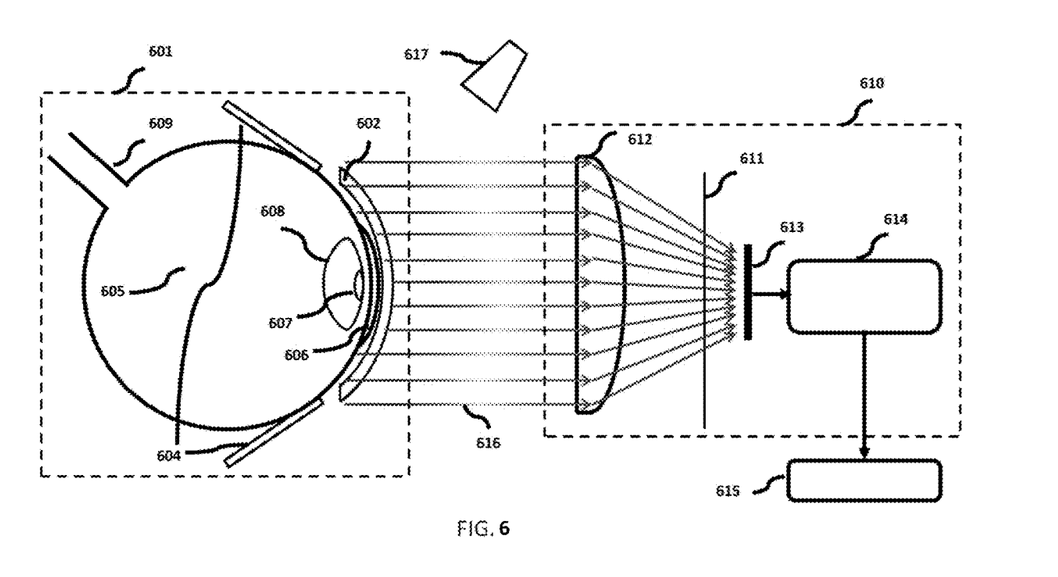
FIG. 6 is a schematic of optical readout system.

In further detail, still referring to the invention of FIG. 6 shows a detailed schematic of the optical readout system (610) for the unpowered, microfluidic pressure sensor (602). (601) embodies the remote sensing object consisting of the vitreous chamber (605) with a lens (608), pupil (607), optical nerve (609), cornea (606) and sclera tissue (604). In one embodiment, typical family living room lighting of 50 lux can be employed as the illumination source (617) to provide the contrast between the sclera and displacing fluids which in pressure-sensitive microfluidic network. As a result, reflected photons (616) from the ocular organ and microfluidic device will be captured by the optical readout system (610). In more detail, (610) contains an image sensor array-such as a CMOS sensor array or charge-coupled device (CCD) (613) along with baseband electronics (614)—such as but not limited to analog-to-digital converters, electronic filters, digital signal processor and microcontroller which can reside on a printed circuit board—to process to information to a diagnosis display (615). An off-the-shelf, digital microscope or commercially available mobile phones with specialized optics hardware and software can be employed to realize (610).

Having described aspects of the invention in detail, it is apparent to one skilled in the art that modifications and variations are possible without departing from the spirit of invention. As various changes could be made in the above constructions, products and methods without departing from the scope of aspects of the invention, it is intended that all matter contained in the above description and shown the accompanying drawings shall be interpreted as illustrative and not in a limiting sense.

What is claimed is:

1. An unpowered, wireless pressure sensor device comprising: a polymer substrate, said polymer substrate encases an optical opening, an injection port and a microfluidic network wherein said injection port installs fluids within said microfluidic network and said microfluidic network includes a sensing chamber network and a sensing channel network for displacement of said fluids, said microfluidic network fluidically coupled to one or more fluidic impedance transformer(s) gradually adjusts the pressure within said microfluidic network and an optical readout system for reading the displacement of said fluids using optical, imaging sensors for said unpowered wireless pressure sensor device.

2. The device of claim 1 wherein said sensing chamber network has lower effective elasticity to applied pressure than said sensing channel network.

3. the device of claim 1, wherein fluidic impedance transformers is installed at the entrance and exit of transitions from the sensing channel and sensing chamber within the microfluidic network.

4. the device of claim 1, wherein said injection port to install the fluids within the microfluidic network before operation.

5. the device of claim 1, wherein said substrate is flexible polymer which is nontoxic and biocompatible consisting of PDMS and PDMS-plastic composites.

6. The device of claim 1, wherein said fluids have low vapour pressure and are biocompatible.

7. The device of claim 1, wherein the pressure sensor device is micromachined.

8. a wireless readout system consisting of an optical imaging system including lens and filters, baseband electronics and digital signal processing algorithms, along with an optical illumination source for said device of claim 1.

* * * * *